United States Patent [19]
Caggiano

[11] 4,021,941
[45] May 10, 1977

[54] DISPOSABLE FOOTWEAR

[76] Inventor: John J. Caggiano, 3965 Monticello Ave., Bronx, N.Y. 10466

[22] Filed: June 22, 1976

[21] Appl. No.: 698,327

[52] U.S. Cl. .................................................. 36/10
[51] Int. Cl.² .......................................... A43B 3/10
[58] Field of Search ............... 36/9 R, 9 A, 1, 3 R, 36/3 A, 10; 2/239

[56] References Cited
UNITED STATES PATENTS

| | | | |
|---|---|---|---|
| 1,659,171 | 2/1928 | Spafford | 36/10 |
| 3,032,898 | 5/1962 | Servin | 36/9 R |
| 3,243,901 | 4/1966 | Clarizio | 36/10 |
| 3,417,408 | 12/1968 | Caggiano | 36/10 |

Primary Examiner—Patrick D. Lawson

[57]. ABSTRACT

A disposable sock body includes plural vertically spaced apart generally horizontal lines of perforation for facilitating removal of selected upper portions of the body and thereby altering the height of the sock body. An absorbent foot pad is provided for selectively receiving medicament to be applied to the sole of the wearer's foot and plural strips of absorbent material are adhered to the exterior of the sock body for selectively receiving a liquid insect repellant. Randomly disposed holes may also be included to provide ventilation.

1 Claim, 5 Drawing Figures

DISPOSABLE FOOTWEAR

FIELD OF THE INVENTION

The present invention relates generally to disposable footwear of the type having plural rings of perforation for facilitating changing the height of the leg engaging portion thereof. In its particular aspects the present invention relates to the provision of an absorbent pad adhered within the footwear for selectively receiving medicament to be applied to the sole of the foot of the user.

BACKGROUND OF THE INVENTION

My previous U.S. Pat. No. 3,417,408, issued Dec. 24, 1968 disclosed a disposable sock body having plural lines or rings of perforation for facilitating removal of selected upper portions thereof to change the height of the body. The disposable sock body then disclosed has been found quite useful for most purposes, but did not deal with the problem of applying medicament to the sole of the foot of the user. Further, there was a problem of insects attacking the disposable material.

OBJECTS OF THE INVENTION

It is an object of the present invention to provide a disposable sock body of the type having plural lines of perforations which body includes pad means for applying medicament to the sole of the foot of the user.

It is a further object of the present invention to provide a sock body which has absorbent pad means adhered thereto for carrying a liquid insect repellant.

SUMMARY OF THE INVENTION

Briefly, the aforementioned and other objects of the present invention are satisfied by providing a disposable sock body of the aforementioned type which includes an absorbent pad adhered along a bottom interior wall of the body for receiving medicament to be applied to the sole of the foot of the wearer.

Further, plural strips of absorbent material are adhered to the exterior of the sock body for carrying a liquid insect repellant.

Other objects, features and advantages of the present invention will become apparent upon perusal of the following detailed description of the preferred embodiment thereof when taken in conjunction with the appended drawing wherein.

DETAILED DESCRIPTION

Figure 1:
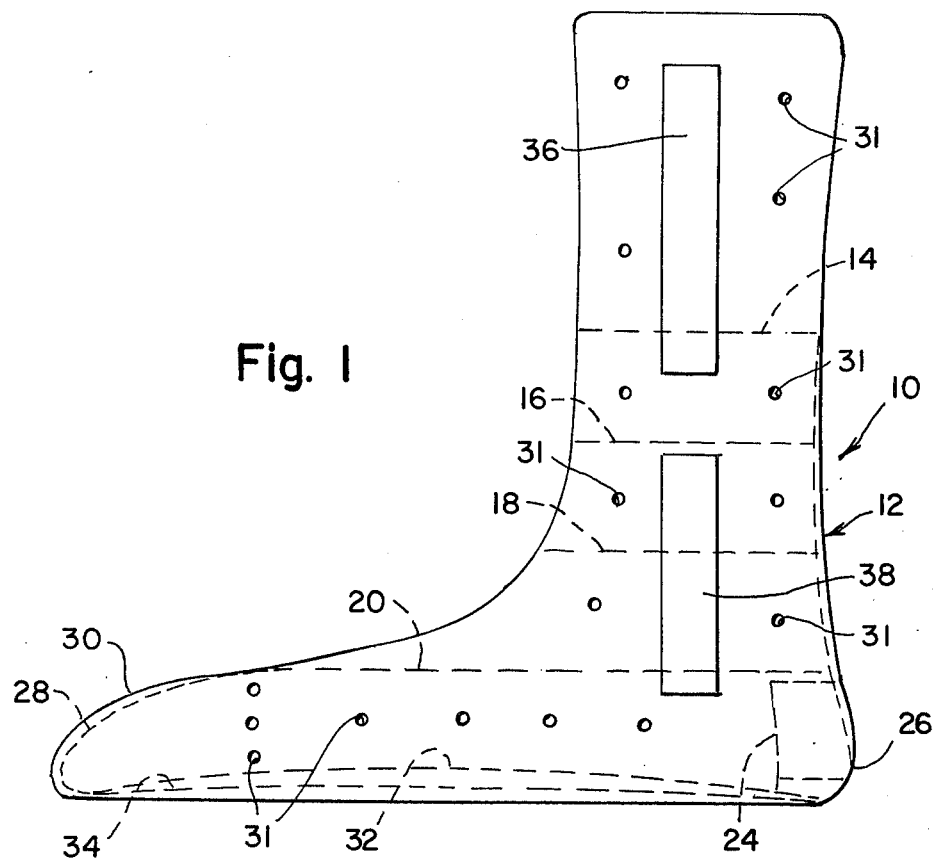
FIG. 1 is a side elevational view of the disposable footwear of the present invention.
Figure 2:
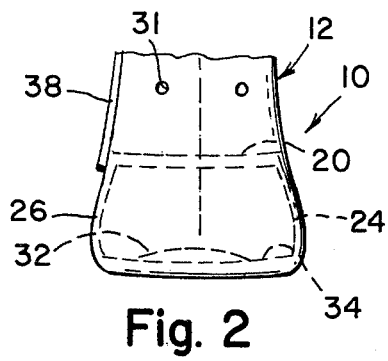
FIG. 2 is a fragmentary back view of a bottom portion of the footwear in FIG. 1.
Figure 3:
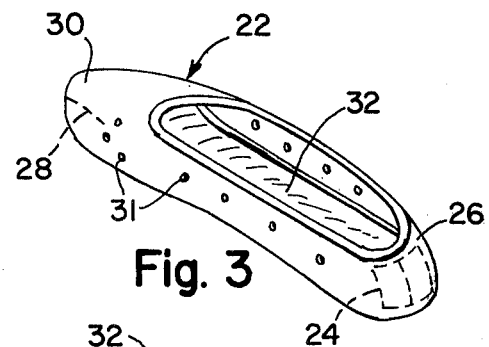
FIG. 3 is a perspective view of a ped removed from the footwear in FIG. 1.
Figure 4:
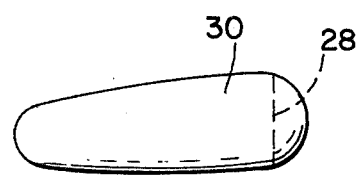
FIG. 4 is a front view of a toe portion of the footwear in FIG. 1.
Figure 5:
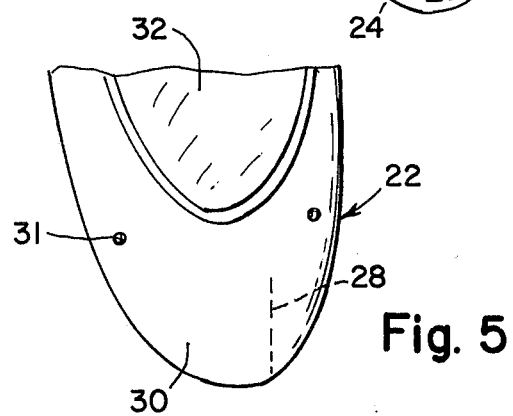
FIG. 5 is a fragmentary top view of the toe portion of the ped in FIG. 3.

Referring to FIGS. 1 and 2 of the drawing there is illustrated disposable footwear 10 similar to any aforementioned previous patent. The footwear 10, which is constructed of disposable material such as paper, is essentially a sock body 12 having plural vertically spaced apart leg encircling rings of perforation 14, 16, 18 and 20 in the sock body to facilitate upper portions of the body being torn off to change the height of the sock body. For example, by tearing along the lowest ring of perforation 20, a ped 22 illustrated in FIG. 3 remains. Further, a perforated generally rectangular contour 24 is provided at the heel 26 of the sock body 12 to facilitate the selective provision of an open heel and a line of perforation 28 is provided in the toe 30 of sock body 12 to enable the top to be parted for selectively receiving a thong (not shown) between the big toe and the remaining toes. Randomly disposed holes 31 may also be included to provide ventilation.

According to the principles of the present invention, an absorbent foot pad 32 is adhered along the bottom interior wall 34 of sock body 12 for receiving medicament, such as for treatment of athlete's foot, for application to the sole of the foot of the user. Further, a pair of vertically spaced apart elongated strips 36 and 38 of absorbent material are adhered to the exterior of the body 12 for selectively receiving liquid insect repellant to be evaporated for protecting the sock body 12 from being attacked by insects.

While the preferred embodiment of the present invention has been described in specific detail it should be understood that numerous modifications, additions and omissions in the details thereof are possible within the intended spirit and scope of the invention claimed herein.

What is claimed is:

1. Footwear comprising a sock body of disposable material having a plural generally vertically spaced apart generally horizontal lines of perforation in its wall for facilitating removal of selected upper portions of said sock body for changing the height of said body; a foot pad of absorbent material adhered along a bottom interior wall of said sock body for receiving medicament for application to the sole of the foot of the user; and a strip of absorbent fragrant material adhered along a portion of the exterior of said sock body for receiving a liquid insect repellant.

* * * * *